United States Patent
Noerenberg et al.

(10) Patent No.: US 6,248,892 B1
(45) Date of Patent: Jun. 19, 2001

(54) PROCESS FOR PREPARING ARYLPYRIDINES

(75) Inventors: Antje Noerenberg, Buettelborn; Steffen Haber, Koenigstein; Andreas Meudt, Floersheim-Weilbach, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/346,429

(22) Filed: Jul. 1, 1999

(30) Foreign Application Priority Data

Jul. 11, 1998 (DE) ............................................ 198 31 246

(51) Int. Cl.$^7$ ...................... C07D 211/72; C07D 211/82; C07D 213/89; B01J 23/745
(52) U.S. Cl. .......................... 546/290; 546/286; 546/301; 546/303; 546/304; 502/338; 502/339
(58) Field of Search ...................................... 546/345, 346, 546/290, 286, 288, 301, 302, 303, 304, 138; 502/339, 338

(56) References Cited

U.S. PATENT DOCUMENTS 5,877,190  3/1999  Dhainaut et al. .

FOREIGN PATENT DOCUMENTS 0834508  4/1998  (EP) .
WO 96/21647  7/1996  (WO) .

OTHER PUBLICATIONS

Derwent Patent Family Report and/or Abstract.
"A Regiospecific Synthesis of Carbosubstituted Heteroarmoatic Derivates Via Pd–Catalyzed Cross Coupling," E. Negishi, F. Luo, R. Frisbee, and H. Matsushita, *Heterocycles*, vol. 18, 1982, pp. 117–122.
"Preparation of π–Deficient Heteroarylzinc Halides by Oxidative Addition of Active Zinc and Its Palladium–Catalyzed Reaction," T. Sakamoto, Y. Kondo, N. Murata, and H. Yamanaka, *Tetrahedron*, vol. 49, No. 43, pp. 9713–9720.
"Palladium Catalysed Coupling of Halobenzenes With Arylboronic Acids: Rôle of the Triphenylphosphine Ligand," D. O'Keefe, M. Dannock and S. Marcuccio, *Tetrahedron Letters*, vol. 33, No. 44, 1992, pp. 6679–6680.
Comparative Study of 1,1'–Bis(diphenylphosphino) cobaltocenium Hexafluorophosphate and 1,1'–Bis(diphenylphosphino) ferrocene as Bidentate Ligands; *Inorganic Chemistry*, vol. 17, No. 10, 1978, pp. 2859–2863, American Chem. Soc.
EPO Search Report—EP Application No. 99112438.9.
"Palladium–Catalyzed Selective Synthesis of Unsymmetrical Biaryls from Aryl Halides or Triflates and Organomanganese Reagents" *Tetrahedron*, vol. 38, No. 25 pp. 4397–4400.
"Control of Reactive Site in Palladium–Catalyzed Grignard Cross–Coupling of Arenes Containing both Bromide and Triflate" *Tetrahedron*, vol. 38, No. 40, pp. 7087–7090.
Chemical Abstracts, vol. 120, No. 3, Jan. 17, 1994 , No. 30634.
Chemical Abstracts, vol. 116, No. 5, Feb. 3, 1992, No. 40986.
Joseph A. Miller et al ; Tetrahedro Letters vol 39, 1998 pp. 7275–7278, Jun. 15, 1998.*
Howard Edan katz; Chelate and Macrocycle effects . . . ; Journal of Organic Chemistry 1985 vol 50, pp. 2086–2091, Dec. 1984.*

* cited by examiner

*Primary Examiner*—Alan L. Rotman
*Assistant Examiner*—Rita Desai
(74) *Attorney, Agent, or Firm*—Scott E. Hanf

(57) ABSTRACT

2-, 3- or 4-arylpyridines are prepared by reacting a halopyridine with an aryl Grignard compound, where the halogen is chlorine or bromine, in the presence of a palladium catalyst of the formula (IV)

(IV)

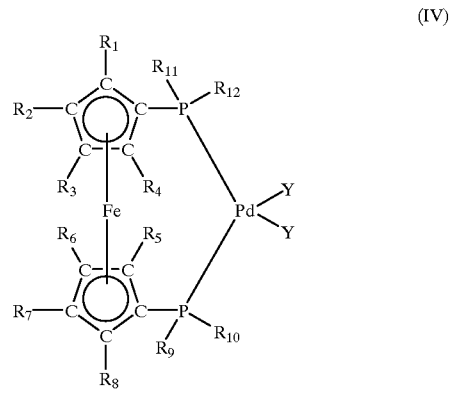

11 Claims, No Drawings

PROCESS FOR PREPARING ARYLPYRIDINES

BACKGROUND OF THE INVENTION

The present invention relates to a novel process for preparing arylpyridines from halopyridines and aryl Grignard reagents using a phosphino-palladium-ferrocene catalyst. Arylpyridines have industrial importance as precursors for active compounds in the agricultural sector.

A method frequently employed for synthesizing arylpyridines on a laboratory scale is palladium-catalyzed cross coupling in which iodoaromatics and bromoaromatics are reacted with organometallic aryl derivatives, in particular arylboronic acids or aryl Grignard reagents, in the presence of palladium or nickel catalysts. Examples describing this methodology may be found, for example, in E. Negishi, F.-T. Luo, R. Frisbee, H. Matsushita, Heterocycles 18, 1982, 117; T. Sakamoto, Y. Kondo, N. Murata, H. Yamanaka, Tetrahedron 49,1993, 9713, EP 0 834 508 A1 and WO 96/21647.

Despite the many publications in the field of synthesis of arylpyridines in the presence of nickel or palladium catalysts, no examples of a relatively large scale industrial implementation of the methods have been known up to now. This can be attributed to the fact that the catalyst systems described frequently require uneconomical amounts of catalyst or give low selectivities, i.e. high proportions of dimerization products. Moreover, large amounts of catalyst, generally >1 mol %, have to be added to achieve industrially usable conversions. In addition, owing to the complexity of the reaction mixtures, no simple recycling of the catalyst is possible, so that catalyst costs generally prevent industrial implementation.

Furthermore, in the Suzuki coupling, substituted biphenyls are found when using customary catalyst systems such as Pd(Oac)$_2$/triphenylphosphine mixtures, due to aryl transfers as seco ary reaction (D. F. O'Keefe et al., TeTrahedron Letters 1992, 6679).

SUMMARY OF THE INVENTION

The present invention relates to a novel process for preparing arylpyridines from halopyridines and aryl Grignard reagents using a phosphino-palladium-ferrocene catalyst.

DESCRPTION OF THE PREFERRED EMBODIMENTS

For the reasons mentioned, it is of great industrial interest to find better, industrially usable catalyst systems for the synthesis of arylpyridines, in particular for the arylation of economically advantageous bromopyridines and chloropyridines. There is therefore a great need for a process which avoids the disadvantages described and makes it possible to obtain arylpyridines in high purity in a technically simple manner.

This object is achieved by a process for preparing arylpyridines of the formula (I)

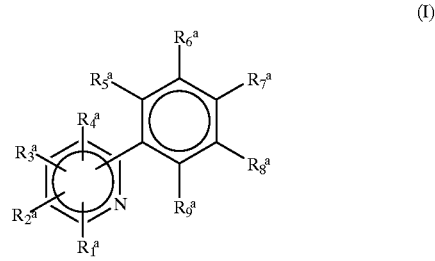

(I)

where
$R_{1a}$ to $R_{9a}$ are identical or different and are hydrogen, $C_1$–$C_{12}$-alkyl, $C_2$–$C_{12}$-alkenyl, $C_2$–$C_{12}$-alkynyl, $C_1$–$C_{12}$-alkoxy, $C_1$–$C_{12}$-acyloxy, O-phenyl, O-benzyl, aryl, heteroaryl, F, Cl, $NO_2$, CN, $SO_2R$, SOR, where R is aryl, preferably phenyl or naphthyl, F or $C_nF_{2n+1}$ where n=1–12, NH($C_1$–$C_6$-alkyl), N($C_1$–$C_6$-alkyl)$_2$, CH=N($C_1$–$C_6$-alkyl), $CX_3$, where X=F, Cl or Br, COO-($C_1$–$C_{12}$-alkyl), CO-($C_1$–$C_{12}$-alkyl), CO-phenyl, COO-phenyl, CON($C_1$–$C_8$-alkyl)$_2$, CONH($C_1$–$C_8$-alkyl), CHCHCOO-($C_1$–$C_{12}$-alkyl), PO(phenyl)$_2$, PO-($C_1$–$C_8$-alkyl)$_2$ or $PO_3$-($C_1$–$C_8$-alkyl)$_2$, which comprises reacting a halopyridine of the formula (II)

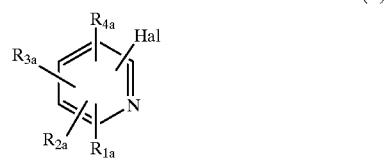

(II)

with an aryl Grignard compound of the formula (III)

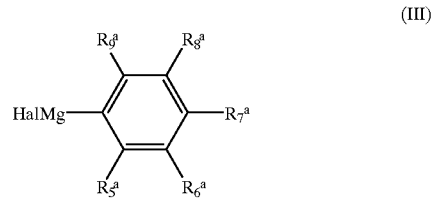

(III)

where Hal is chlorine or bromine, in the presence of a palladium catalyst of the formula (IV)

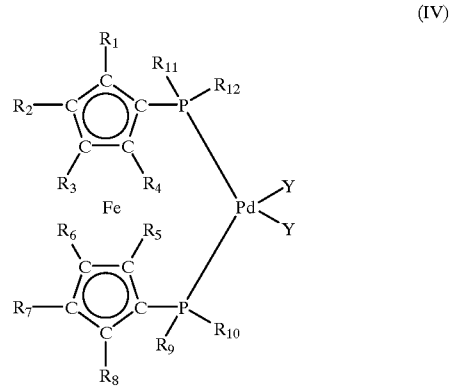

(IV)

where

R$_1$ to R$_8$ are identical or different and are hydrogen, C$_1$–C$_4$-alkyl, C$_5$–C$_8$-cycloalkyl, C$_1$–C$_4$-alkoxy, fluorine, NH$_2$, NH-(C$_1$–C$_4$-alkyl), N(C$_1$–C$_4$-alkyl)$_2$, CO$_2$-alkyl-(C$_1$–C$_4$) or phenyl, or R$_1$, and R$_2$, or R$_2$ and R$_3$, or R$_3$ and R$_4$; and/or R$_5$ and R$_6$, or R$_6$ and R$_7$, or R$_7$ and R$_8$ together form an aliphatic or aromatic ring, R$_9$ to R$_{12}$ are identical or different and are C$_1$–C$_8$-alkyl, C$_3$–C$_{12}$-cycloalkyl or aryl, which may be substituted by from 1 to 3 substituents selected from the group consisting of C$_1$–C$_4$-alkyl, C$_1$–C$_4$-alkoxy and halogen, and Y is an anion of an organic or inorganic acid.

The compound of the formula (I) can be a 2-, 3- or 4-arylpyridine.

Preference is given to a process for preparing compounds of the formula (I), in which R$_{1a}$ to R$_{9a}$ are hydrogen, C$_1$–C$_8$-alkyl, C$_2$–C$_8$-alkenyl, C$_2$–C$_8$-alkynyl, C$_1$–C$_8$-alkoxy, C$_1$–C$_8$-acyloxy, F, Cl, CN, O-phenyl, phenyl, a 5- or 6-membered heteroaryl having from 1 to 3 heteroatoms selected from the group consisting of O, S and N, COO-(C$_1$–C$_8$-alkyl), CO-(C$_1$–C$_8$-alkyl), CHCHCOO-(C$_1$–C$_8$-alkyl), CONH(C$_1$–C$_4$-alkyl) or CON(C$_1$–C$_4$-alkyl)$_2$.

Particular preference is given to a process for preparing compounds of the formula (I) in which R$_{1a}$ to R$_{9a}$ are hydrogen, C$_1$–C$_4$-alkyl, C$_1$–C$_4$-alkoxy, CN, COO(C$_1$–C$_4$-alkyl), phenyl, thiophenyl, furanyl, imidazolyl, oxadiazolyl, thiadiazolyl, oxazolyl, 4,5-dihydrooxazolyl, pyridyl, CONH(C$_1$–C$_2$-alkyl), CON(C$_1$–C$_2$-alkyl)$_2$, F or Cl.

A process for preparing 2-phenylpyridine is of very particular interest.

Preference is given to catalysts of the formula (IV), in which R$_1$ to R$_8$ are hydrogen, methyl, ethyl, C$_5$–C$_6$-cycloalkyl, methoxy, ethoxy, fluorine, NH(C$_1$–C$_2$-alkyl), N(C$_1$–C$_2$-alkyl)$_2$ or phenyl, and R$_9$, R$_{10}$, R$_{11}$, R$_{12}$ are phenyl, tolyl, xylyl, mesityl, fluorophenyl or (C$_1$–C$_4$)-alkoxyphenyl, and Y is chloride, bromide, iodide, fluoride, acetate, propionate benzoate, sulfate, hydrogensulfate, nitrate, phosphate, tetrafluoroborate, tosylate, mesylate, acetylacetonate, hexafluoroacetylacetonate or pyrazolyl.

Particular preference is given to compounds of the formula (IV) in which R$_1$ to R$_8$ are H, methyl or phenyl, and R$_9$ to R$_{12}$ are phenyl, tolyl, xylyl, fluorophenyl or methoxyphenyl.

Very particular preference is given to 1,1'-bis (diphenylphosphino)ferrocenepalladium(II) chloride (=Pd (dppf)Cl$_2$), 1,1'-bis(diphenylphosphino)ferrocenepalladium (II) chloride•dichloromethane and 1,1'-bis (diphenylphosphino)ferrocenepalladium(II) bromide.

The catalyst is advantageously used in an amount corresponding to from 0.00001 to 1 times, preferably 0.0001 to 0.1 times, in particular from 0.0001 to 0.08 times, the molar amount of halopyridine of the formula (II)

The catalyst is preferably used in a homogeneous phase.

Solvents used are generally inert organic solvents. Preference is given to using aromatic, polar aprotic solvents such as alkylbenzenes, dialkylbenzenes or trialkylbenzenes, or ethers such as tetrahydrofuran, tert-butyl methyl ether or diethyl ether.

The palladium catalysts used can be synthesized prior to the reaction according to the invention, but they can also be generated in situ without loss of catalytic activity. The synthesis of the catalyst is carried out, for example, by a method analogous to that described by A. W. Rudie, D. W. Lichtenberg, M. L. Katcher, A. Davison, Inorg. Chem. 17, 1978, 2859.

The process of the invention is generally carried out at temperatures of from 20 to 200° C. Preference is given to temperatures of from 60 to 180° C., in particular from 60 to 100° C.

It is particularly advantageous to meter the Grignard component, dissolved in an inert solvent, into the haloaromatic and the catalyst in a solvent which is inert toward all reactants. Suitable inert solvents are preferably those mentioned above for the catalyst.

The Grignard compounds used are advantageously used as 15–40% strength by weight solutions in tetrahydrofuran. 20–35% strength by weight solutions in tetrahydrofuran are particularly advantageous.

The molar ratios of the halopyridines of the formula (II) and the Grignard compounds of the formula (III) are advantageously from 1:1 to 1:1.3, preferably from 1:1.001 to 1:1.01.

Especially 2-phenylpyridine and its derivatives can be prepared with the aid of the process of the invention in yields of greater than 95% and with conversions and selectivities of >98%. By-products formed during the reaction by dimerization of the Grignard components or dimerization of the halopyridines or by subsequent reactions of the 2-phenylpyridines with excess Grignard reagent are observed only to a minor extent (<1%).

The compounds required as starting materials are known and can be prepared by methods known per se.

EXAMPLES

Example 1

216.5 g (3.0 mol) of tetrahydrofuran (THF), 113.5 g (1.0 mol) of 2-chloropyridine and 0.24 g of Pd(dppf)Cl$_2$ (0.03 mol %) are placed in a flask and heated to 50° C. while stirring. 510 g of phenylmagnesium chloride solution in THF (27% strength) are slowly metered in while cooling externally so that the temperature does not exceed 50° C. The mixture is then stirred for another 90 minutes at this temperature. It is slowly hydrolyzed with 250 g of water and allowed to cool to room temperature. After phase separation, the aqueous phase is stirred with 250 ml of tert-butyl methyl ether. After renewed phase separation, the organic phases combined and the reaction mixture is evaporated at 150 mbar. It is subsequently distilled at atmospheric pressure until a bottom temperature of 80° C. has been reached. The distillation residue is distilled at 10 mbar, giving 152.0 g of 2-phenylpyridine (98.1%), purity: 98.7% (according to GC).

Examples 2 to 4

Using a method analogous to Example 1, the following compounds are synthesized according to the invention from the corresponding starting compounds:

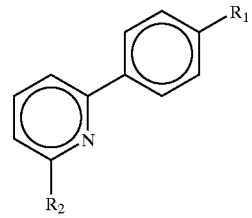

| Example | R$_1$ | R$_2$ |
|---|---|---|
| 2 | Cl | H |
| 3 | H | CH$_3$ |
| 4 | CH$_3$ | CH$_3$ |

The yields are in each case >95% and the selectivity (according to GC) is greater than 98%.

What is claimed is:
1. A process for preparing arylpyridines of the formula (I)

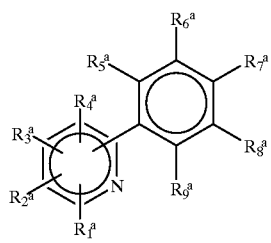

(I)

where $R_{1a}$ to $R_{9a}$ are identical or different and are hydrogen, $C_1$–$C_{12}$-alkyl, $C_2$–$C_{12}$-alkenyl, $C_2$–$C_{12}$-alkynyl, $C_1$–$C_{12}$-alkoxy, $C_1$–$C_{12}$-acyloxy, aryl, F, Cl, CN, $CX_3$, where X=F, Cl or Br, and CHCHCOO-($C_1$–$C_{12}$-alkyl), which comprises reacting a halopyridine of the formula (II)

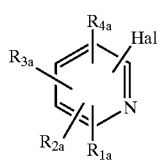

(II)

with an aryl Grignard compound of the formula (III)

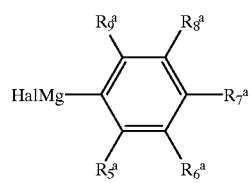

(III)

where Hal is chlorine or bromine, in the presence of a palladium catalyst of the formula (IV)

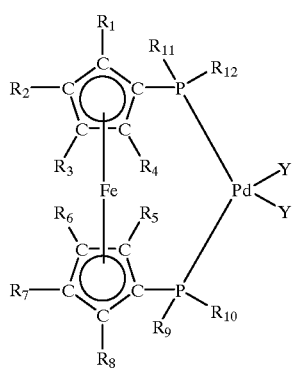

(IV)

where $R_1$ to $R_8$ are identical or different and are hydrogen, $C_1$–$C_4$-alkyl, $C_5$–$C_8$-cycloalkyl, $C_1$–$C_4$-alkoxy, fluorine, $NH_2$, NH-($C_1$–$C_4$-alkyl), N($C_1$–$C_4$-alkyl)$_2$, $CO_2$-alkyl-($C_1$–$C_4$) or phenyl, or $R_1$ and $R_2$, or $R_2$ and $R_3$, or $R_3$ and $R_4$; $R_5$ and $R_6$, or $R_6$ and $R_7$, or $R_7$ and $R_8$ together form an aliphatic or aromatic ring, $R_9$ to $R_{12}$ are identical or different and are $C_1$–$C_8$-alkyl, $C_3$–$C_{12}$-cycloalkyl or aryl, which are optionally substituted by from 1 to 3 substituents selected from the group consisting of $C_1$–$C_4$-alkyl, $C_1$–$C_4$-alkoxy and halogen, and Y is an anion selected from the group of an organic acid, an inorganic acid and pyrazolyl.

2. The process as claimed in claim 1, wherein $R_{1a}$ to $R_{9a}$ are hydrogen, $C_1$–$C_8$-alkyl, $C_2$–$C_8$-alkenyl, $C_2$–$C_8$-alkynyl, F, Cl, CN, phenyl, CHCHCOO-($C_1$–$C_8$-alkyl).

3. The process as claimed in claim 1, wherein $R_{1a}$ to $R_{9a}$ are hydrogen, $C_1$–$C_4$-alkyl, CN, phenyl, F or Cl.

4. The process as claimed in claim 1, wherein the compound of the formula (I) is 2-phenylpyridine.

5. The process as claimed in claim 1, wherein, in the compound of the formula (IV)

$R_1$ to $R_8$ are hydrogen, methyl, ethyl, $C_5$–$C_6$-cycloalkyl, methoxy, ethoxy, fluorine, NH($C_1$–$C_2$-alkyl), N($C_1$–$C_2$-alkyl)$_2$ or phenyl, and $R_9$, $R_{10}$, $R_{11}$, $R_{12}$ are phenyl, tolyl, xylyl, mesityl, fluorophenyl or $C_1$–$C_4$-alkoxyphenyl, and Y is chloride, bromide, iodide, fluoride, acetate, propionate, benzoate, sulfate, hydrogensulfate, nitrate, phosphate, tetrafluoroborate, tosylate, mesylate, acetylacetonate, hexafluoroacetylacetonate or pyrazolyl.

6. The process as claimed in claim 1, wherein, in the compound of the formula (IV)

$R_1$ to $R_8$ are H, $CH_3$ or phenyl, and $R_9$ to $R_{12}$ are phenyl, tolyl, xylyl, fluorophenyl or methoxyphenyl.

7. The process as claimed in claim 1, wherein the catalyst of the formula (IV) is 1,1'-bis(diphenylphosphino)ferrocenepalladium(II) chloride, 1,1'-bis(diphenylphosphino)ferrocenepalladium(II) chloride•dichloromethane or 1,1'-bis(diphenylphosphino)ferrocenepalladium(II) bromide.

8. The process as claimed in claim 1, wherein the catalyst of the formula (IV) is used in an amount corresponding to from 0.00001 to 1 times, the molar amount of the halopyridine of the formula (II).

9. The process as claimed in claim 1, wherein the reaction is carried out in an aromatic, polar aprotic solvent or an ether.

10. The process as claimed in claim 1, wherein the aryl Grignard compound of the formula (III) is dissolved in an inert solvent and metered into the halopyridine of the formula (II) and the catalyst of the formula (IV).

11. The process as claimed in claim 1, wherein the catalyst of the formula (IV) is used in an amount corresponding to from 0.0001 to 0.1 times, the molar amount of the halopyridine of the formula (II).

* * * * *